(12) United States Patent
Klubben, III et al.

(10) Patent No.: US 10,582,843 B2
(45) Date of Patent: Mar. 10, 2020

(54) ILLUMINATING SURGICAL DEVICE HAVING LIGHT DIFFUSING FIBER

(71) Applicant: Corning Incorporated, Corning, NY (US)

(72) Inventors: William Spencer Klubben, III, Corning, NY (US); Horst Schreiber, Livonia, NY (US)

(73) Assignee: CORNING INCORPORATED, Corning, NY (US)

( * ) Notice: Subject to any disclaimer, the term of this patent is extended or adjusted under 35 U.S.C. 154(b) by 220 days.

(21) Appl. No.: 15/560,000

(22) PCT Filed: Mar. 22, 2016

(86) PCT No.: PCT/US2016/023551
§ 371 (c)(1),
(2) Date: Sep. 20, 2017

(87) PCT Pub. No.: WO2016/154186
PCT Pub. Date: Sep. 29, 2016

(65) Prior Publication Data
US 2018/0064322 A1 Mar. 8, 2018

Related U.S. Application Data

(60) Provisional application No. 62/208,255, filed on Aug. 21, 2015, provisional application No. 62/137,416, filed on Mar. 24, 2015.

(51) Int. Cl.
*A61B 1/07* (2006.01)
*A61B 1/313* (2006.01)
(Continued)

(52) U.S. Cl.
CPC .............. *A61B 1/07* (2013.01); *A61B 1/0653* (2013.01); *A61B 1/3132* (2013.01); *A61B 90/30* (2016.02);
(Continued)

(58) Field of Classification Search
CPC .. A61B 1/07; A61B 1/313; A61B 1/06; A61B 1/0653; A61B 1/3132
See application file for complete search history.

(56) References Cited

U.S. PATENT DOCUMENTS 4,248,214 A 2/1981 Hannah et al.
5,531,741 A 7/1996 Barbacci
(Continued)

FOREIGN PATENT DOCUMENTS

CN 204840698 U 12/2015
CN 106178280 A 12/2016
(Continued)

OTHER PUBLICATIONS

Chacin, F. et al., "The Implications of Lighted Ureteral Stenting in Laparoscopic Colectomy." Journal of the Society of Laparoendoscopic Surgeons, vol. 6, Issue 1, pp. 49-52, Mar. 2002.
(Continued)

*Primary Examiner* — Christopher J Beccia
(74) *Attorney, Agent, or Firm* — John P. Ciccarelli

(57) ABSTRACT

An illumination system for a surgical device is provided. The illumination system includes a tubular body made of a light permeable material and having at least one lumen extending between a distal end and a proximal end. The illumination system further includes a light source. At least one light diffusing optical fiber is disposed in the at least one lumen, the at least one light diffusing optical fiber having a core, primary cladding, and a plurality of nano-sized structures, the optical fiber further including an outer surface, and
(Continued)

an end optically coupled to the light source. The fiber is configured to scatter guided light via the nano-sized structures away from the core and through the outer surface, to form a light-source fiber portion having a length that emits substantially uniform radiation over its length.

27 Claims, 3 Drawing Sheets

(51) Int. Cl.
*A61B 90/30* (2016.01)
*A61B 1/06* (2006.01)
*A61B 90/00* (2016.01)
*A61B 17/02* (2006.01)
*F21V 8/00* (2006.01)

(52) U.S. Cl.
CPC ......... *A61B 17/0218* (2013.01); *A61B 90/361* (2016.02); *A61B 90/37* (2016.02); *G02B 6/0003* (2013.01)

(56) References Cited

U.S. PATENT DOCUMENTS

| | | | |
|---|---|---|---|
| 5,879,306 A | 3/1999 | Fontenot et al. | |
| 5,954,652 A | 9/1999 | Heyman | |
| 6,135,993 A * | 10/2000 | Hussman ............. | A61B 5/0084 606/10 |
| 6,551,346 B2 | 4/2003 | Crossley | |
| 7,041,139 B2 | 5/2006 | Bluni et al. | |
| 8,404,273 B2 | 3/2013 | Baumgart et al. | |
| 8,492,448 B2 | 7/2013 | Dewa et al. | |
| 8,585,681 B2 | 11/2013 | Boenig et al. | |
| 8,779,386 B2 | 7/2014 | Bak | |
| 8,805,141 B2 | 8/2014 | Fewkes et al. | |
| 8,897,611 B2 | 11/2014 | Genier | |
| 8,929,703 B2 | 1/2015 | Logunov et al. | |
| 8,953,914 B2 | 2/2015 | Genier | |
| 8,980,174 B2 | 3/2015 | Haytman et al. | |
| 9,025,923 B2 | 5/2015 | Logunov et al. | |
| 9,039,966 B2 | 5/2015 | Anderson et al. | |
| 9,067,059 B2 | 6/2015 | Bissig et al. | |
| 9,093,003 B2 | 7/2015 | Logunov et al. | |
| 9,217,826 B2 | 12/2015 | Logunov et al. | |
| 9,259,513 B2 | 2/2016 | Bedwell et al. | |
| 9,393,339 B2 | 7/2016 | Park et al. | |
| 9,439,989 B2 | 9/2016 | Lalicki et al. | |
| 9,550,005 B2 | 1/2017 | Lin et al. | |
| 9,795,466 B2 | 10/2017 | Piergallini et al. | |
| 9,808,647 B2 | 11/2017 | Rhodes et al. | |
| 9,925,390 B2 | 3/2018 | Yehezkel | |
| 9,943,379 B2 | 4/2018 | Gregg, II et al. | |
| 10,046,070 B1 | 8/2018 | Zaborsky et al. | |
| 10,166,402 B2 | 1/2019 | Brennan et al. | |
| 10,183,144 B2 | 1/2019 | Tang et al. | |
| 10,241,035 B2 | 3/2019 | Bonnick et al. | |
| 2006/0085052 A1 | 4/2006 | Feuerstein et al. | |
| 2006/0167439 A1 | 7/2006 | Kalser et al. | |
| 2007/0104437 A1 | 5/2007 | Bookbinder et al. | |
| 2009/0257910 A1 | 10/2009 | Segal | |
| 2010/0016844 A1 | 1/2010 | Patel, Jr. | |
| 2010/0268151 A1 | 10/2010 | Mauge et al. | |
| 2011/0122646 A1 | 5/2011 | Bickham et al. | |
| 2012/0275180 A1 | 11/2012 | Button et al. | |
| 2012/0275745 A1 | 11/2012 | Logunov | |
| 2013/0035629 A1 | 2/2013 | Soltz et al. | |
| 2013/0088888 A1* | 4/2013 | Fewkes ................. | G02B 6/001 362/558 |
| 2013/0107565 A1 | 5/2013 | Genier | |
| 2013/0267888 A1 | 10/2013 | Rhodes et al. | |
| 2013/0308335 A1 | 11/2013 | Genier | |
| 2014/0188249 A1 | 7/2014 | Pendleton et al. | |
| 2015/0080709 A1 | 3/2015 | Chaturvedi | |
| 2018/0036443 A1 | 2/2018 | Messerly | |
| 2018/0147417 A1 | 5/2018 | Rantala | |
| 2018/0178031 A1 | 6/2018 | Wu | |
| 2018/0207302 A1 | 7/2018 | Vasilenko | |
| 2018/0304094 A1 | 10/2018 | Hicks et al. | |
| 2018/0326104 A1 | 11/2018 | Hawkins et al. | |

FOREIGN PATENT DOCUMENTS

| | | |
|---|---|---|
| CN | 106178282 A | 12/2016 |
| CN | 105396169 B | 6/2018 |
| CN | 108671243 A | 10/2018 |
| JP | 59155824 A | 9/1984 |
| JP | 05546575 B2 | 7/2014 |
| KR | 1362704 B1 | 2/2014 |
| KR | 1851576 B1 | 4/2018 |
| KR | 2018049757 A | 5/2018 |
| KR | 1892996 B1 | 8/2018 |
| KR | 2018135256 A | 12/2018 |
| KR | 2018135257 A | 12/2018 |
| WO | 1998011462 A1 | 3/1998 |
| WO | 2010011299 A2 | 1/2010 |
| WO | 2012099484 A1 | 7/2012 |
| WO | 2015168129 A1 | 11/2015 |
| WO | 2018009864 A1 | 1/2018 |
| WO | 2019025808 A1 | 2/2019 |

OTHER PUBLICATIONS

International Search Report and Written Opinion of the International Searching Authority; PCT/US2016/023551; dated Jun. 20, 2016; 11 Pages; European Patent Office.

Stryker Corporation, "Stryker Infravision Ureteral Kit." <http://strykercorp.com/en-us/products/Endoscopy/Laparoscopy/AccessoriesandDisposables_OBSOLETE/InfraVisionUreteralKit/index.htm> Originally Retrieved Dec. 10, 2014.

Cook Medical Incorporated, "Bush Ureteral Illuminating Catheter Sets." Urology Product Catalog, pp. 27, 2007.

Office Action dated Jun. 26, 2019 in Corresponding European Patent Application No. 16713709.0, European Patent Office, 5 Pages.

* cited by examiner

ILLUMINATING SURGICAL DEVICE HAVING LIGHT DIFFUSING FIBER

This is a national stage application under 35 U.S.C. § 371 of International Application No. PCT/US2016/023551, filed on Mar. 22, 2016, claims the benefit of priority to U.S. Application No. 62/208,255 filed on Aug. 21, 2015 and to U.S. Application No. 62/137,416 filed on Mar. 24, 2015 the content of which is incorporated herein by reference in its entirety.

FIELD

The present disclosure relates generally to illuminating surgical devices. More particularly, the present disclosure relates to illuminating surgical devices having light diffusing fiber and to methods for illuminating anatomical structures using surgical devices having light diffusing fiber

BACKGROUND

Laparoscopic surgery is a technique which allows traditionally open surgical procedures to be performed in a minimally invasive manner. To perform the procedure, a physician makes several small incisions through which instruments are placed. The instruments include surgical instruments and a laparoscope, which is a specialized camera that allows for visual examination of the interior of a patient. The laparoscope transmits images to video monitors in the operating room, and the physician is able to view the images while manipulating the instruments to perform the specific surgical procedure.

Laparoscopic surgery has been applied to perform many surgeries including, for example, gallbladder removal (cholecystectomy), appendectomy, hernia repair, removal of part of the colon (colectomy) or small intestine, surgery for acid-reflux disease (fundoplication), removal of adrenal glands, and removal of the spleen. Additionally, laparoscopic surgery has been used in multiple gynecologic procedures such as removal of the uterus (laparoscopic hysterectomy), removal of the fibroids (laparoscopic myomectomy), surgical treatment of ovarian cysts (laparoscopic cystectomy), ectopic pregnancy, and treatment of endometriosis and pelvic pain (laparoscopic presacral neurectomy). The technique has also been used to treat lung conditions, such as to remove lung tumors, and also in urological procedures, such as removing kidney cysts, kidney stones, and portions of the prostate.

During laparoscopic surgery, as well as during other explorations and procedures, it can often be difficult for a physician to be aware of the location of specific anatomical structures. It can also be difficult for a physician to distinguish anatomical structures that are the target of the procedure from anatomical structures that should be avoided during the procedure.

Exemplary anatomical structures that should be avoided during some of the procedures mentioned above include the ureters, blood vessels, gastrointestinal passageways, bile ducts, lymph passageways, spinal lumens, bronchial passageways nasal passages, and any other luminal organs. However, during laparoscopic surgery, the physician often has limited vision of the surgical site and lacks the benefit of direct tactile perception which is available with conventional open surgical techniques. As such, there is an increased risk of causing unintended injury during such surgeries.

SUMMARY

According to an embodiment of the present disclosure, an illumination system for a surgical device is provided. The illumination system includes a tubular body made of a light permeable material, the tubular body having a peripheral wall, a distal end, a proximal end, and at least one lumen extending between the distal end and the proximal end. The illumination system further includes a light source that generates light having at least one wavelength between 200 nm and 2000 nm. At least one light diffusing optical fiber is disposed in the at least one lumen, the at least one light diffusing optical fiber having a core, primary cladding, and a plurality of nano-sized structures, the optical fiber further including an outer surface, and an end optically coupled to the light source. The fiber is configured to scatter guided light via the nano-sized structures away from the core and through the outer surface, to form a light-source fiber portion having a length that emits substantially uniform radiation over its length.

According to another embodiment of the present disclosure, a method for illuminating an anatomical structure is provided. The method includes inserting at least a portion of a tubular body into the interior of an anatomical structure, wherein the tubular body is made of a light permeable material. The tubular body includes a peripheral wall, a distal end, a proximal end, and at least one lumen extending between the distal end and the proximal end, the at least one lumen having an opening at the distal end and an opening at the proximal end. The tubular body further includes at least one light diffusing optical fiber disposed in the at least one lumen, the at least one light diffusing optical fiber having a core, primary cladding, and a plurality of nano-sized structures, the optical fiber further including an outer surface, and an end optically coupled to a light source. The fiber is configured to scatter guided light via the nano-sized structures away from the core and through the outer surface, to form a light-source fiber portion having a length that emits substantially uniform radiation over its length. The method further includes introducing light from the light source into the end of the at least one light diffusing optical fiber optically coupled to the light source and emitting the light through the outer surface of the fiber to illuminate the light-source fiber portion over its length.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiment(s), and together with the description serve to explain principles and operation of the various embodiments.

BRIEF DESCRIPTION OF THE DRAWINGS

The disclosure will be understood more clearly from the following description and from the accompanying figures, given purely by way of non-limiting example, in which.

DETAILED DESCRIPTION

Figure 1:
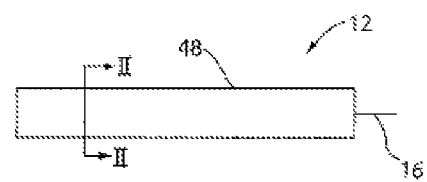
FIG. 1 is a schematic side view of a section of an example embodiment of light-diffusing optical fiber.

Reference will now be made in detail to the present embodiment(s), an example(s) of which is/are illustrated in the accompanying drawings. Whenever possible, the same reference numerals will be used throughout the drawings to refer to the same or like parts.

The singular forms "a," "an" and "the" include plural referents unless the context clearly dictates otherwise. The endpoints of all ranges reciting the same characteristic are independently combinable and inclusive of the recited endpoint. All references are incorporated herein by reference.

According to an embodiment of the present disclosure, an surgical device is provided. The surgical device includes at least one light diffusing optical fiber which facilitates illumination of anatomical structures in a manner that increases the visibility of the anatomical structures to an operator, such as a physician, performing surgery.

The illumination system includes at least one light diffusing optical fiber disposed in the at least one lumen of a tubular body. The at least one light diffusing optical fiber includes a core, a primary cladding, and a plurality of nano-sized structures. The optical fiber further includes an outer surface, and an end optically coupled to a light source. The light diffusing optical fiber may be configured to scatter guided light via the nano-sized structures away from the core and through the outer surface, to form a light-source fiber portion having a length that emits substantially uniform radiation over its length.

The term "flexible light diffusing waveguide" refers to a flexible optical waveguide, such as an optical fiber, employing nano-sized structures that are utilized to scatter or diffuse light out of the sides of the fiber, such that light is guided away from the core of the waveguide and through the outer surfaces of the waveguide to provide illumination. Concepts relevant to the underlying principles of the claimed subject matter are disclosed in U.S. Patent Application Publication No. US 2011/0122646 A1, which is incorporated in its entirety herein by reference.

The term "light source" refers to a laser, light emitting diode or other component capable of emitting electromagnetic radiation that is either in the visible light range of wavelengths or is of a wavelength that can interact with a luminophore to emit light in the visible light wavelength range.

The term "luminophore" refers to an atom or chemical compound that manifests luminescence, and includes a variety of fluorophores and phosphors.

The following terms and phrases are used in connection with light diffusing fibers having nano-sized structures.

The "refractive index profile" is the relationship between the refractive index or the relative refractive index and the waveguide (fiber) radius.

The "relative refractive index percent" is defined as $$\Delta(r)\% = 100 \times [n(r)^2 - n_{REF}^2]/2n(r)^2,$$

where n(r) is the refractive index at radius r, unless otherwise specified. The relative refractive index percent is defined at 850 nm unless otherwise specified. In one aspect, the reference index $n_{REF}$ is silica glass with a refractive index of 1.452498 at 850 nm, in another aspect it is the maximum refractive index of the cladding glass at 850 nm. As used herein, the relative refractive index is represented by $\Delta$ and its values are given in units of "%", unless otherwise specified. In cases where the refractive index of a region is less than the reference index $n_{REF}$, the relative index percent is negative and is referred to as having a depressed region or depressed-index, and the minimum relative refractive index is calculated at the point at which the relative index is most negative unless otherwise specified. In cases where the refractive index of a region is greater than the reference index $n_{REF}$, the relative index percent is positive and the region can be said to be raised or to have a positive index.

An "updopant" is herein considered to be a dopant which has a propensity to raise the refractive index relative to pure undoped $SiO_2$. A "downdopant" is herein considered to be a dopant which has a propensity to lower the refractive index relative to pure undoped $SiO_2$. An updopant may be present in a region of an optical fiber having a negative relative refractive index when accompanied by one or more other dopants which are not updopants. Likewise, one or more other dopants which are not updopants may be present in a region of an optical fiber having a positive relative refractive index. A downdopant may be present in a region of an optical fiber having a positive relative refractive index when accompanied by one or more other dopants which are not downdopants.

Likewise, one or more other dopants which are not downdopants may be present in a region of an optical fiber having a negative relative refractive index.

The term "a-profile" or "alpha profile" refers to a relative refractive index profile, expressed in terms of $\Delta(r)$ which is in units of "%", where r is radius, which follows the equation, $$\Delta(r) = \Delta(r_o)(1 - [|r - r_o|/(r_1 - r_o)]^\alpha),$$

where $r_o$ is the point at which $\Delta(r)$ is maximum, $r_1$ is the point at which $\Delta(r)$ % is zero, and r is in the range $r_1 \leq r \leq r_f$, where $\Delta$ is defined above, $r_1$ is the initial point of the a-profile, $r_f$ is the is final point of the a-profile, and $\alpha$ is an exponent which is a real number.

As used herein, the term "parabolic" therefore includes substantially parabolically shaped refractive index profiles which may vary slightly from an $\alpha$ value of 2.0 at one or more points in the core, as well as profiles with minor variations and/or a centerline dip. In some exemplary embodiments, $\alpha$ is greater than 1.5 and less than 2.5, more preferably greater than 1.7 and less than 2.3 and even more preferably between 1.8 and 2.3 as measured at 850 nm. In other embodiments, one or more segments of the refractive index profile have a substantially step index shape with an $\alpha$ value greater than 8, more preferably greater than 10 even more preferably greater than 20 as measured at 850 nm.

The term "nano-structured fiber region" describes a fiber having a region or area with a large number of gas filled voids, or other nano-sized structures. The region or area may have, for example, more than 50 voids, or more than 100 voids, or even more than 200 voids in the cross-section of the fiber. The gas filled voids may contain, for example, $SO_2$, Kr, Ar, $CO_2$, $N_2$, $O_2$, or mixture thereof. The cross-sectional size (e.g., diameter) of nano-sized structures (e.g., voids) as described herein may vary from about 10 nm to about 1.0 µm (for example, from about 50 nm to about 500 nm), and the length may vary from about 1.0 millimeter to about 50 meters (for example, from about 2.0 mm to about 5.0 meters, or from about 5.0 mm to about 1.0 meters).

In standard single mode or multimode optical fibers, the losses at wavelengths less than 1300 nm are dominated by Rayleigh scattering. These Rayleigh scattering losses $L_s$ are determined by the properties of the material and are typically about 20 dB/km for visible wavelengths (400-700 nm). Rayleigh scattering losses also have a strong wavelength dependence (i.e., $L_S \propto 1/\lambda^4$, see FIG. 4B, comparative fiber A), which means that at least about 1.0 km to about 2.0 km of the fiber is needed to dissipate more than 95% of the input light. Shorter lengths of such fiber would result in lower illumination efficiency, while using long lengths (about 1.0 km to about 2.0 km, or more) can be more costly and can be difficult to manage.

In certain configurations of lighting applications it is desirable to use shorter lengths of fiber, for example, having a length of about 0.02 meters to about 100 meters. This requires an increase of scattering loss from the fiber, while being able to maintain good angular scattering properties (uniform dissipation of light away from the axis of the fiber) and good bending performance to avoid bright spots at fiber bends. A desirable attribute of at least some of the embodiments described herein is uniform and high illumination along the length of the fiber illuminator. Because the optical fiber is flexible, it allows a wide variety of the illumination shapes to be deployed. It is preferable to have no bright spots (due to elevated bend losses) at the bending points of the fiber, such that the illumination provided by the fiber does not vary by more than about 30%, preferably by less than about 20% and more preferably by less than about 10%. For example, in at least some embodiments, the average scattering loss of the fiber is greater than about 50 dB/km, and the scattering loss does not vary more than about 30% (i.e., the scattering loss is within ±30% of the average scattering loss) over any given fiber segment having a length of about 0.2 meters. The average scattering loss of the fiber may be greater than about 50 dB/km with the scattering loss varying by less than about 30% over fiber segments of having a length of less than about 0.05 meters. The average scattering loss of the fiber may be greater than about 50 dB/km with the scattering loss varying by less than about 30% over fiber segments having a length of about 0.01 meters. The average scattering loss of the fiber may also be greater than about 50 dB/km with the scattering loss varying by less than about 20%, and preferably by less than about 10% over fiber segments having a length of about 0.01 meters.

According to embodiments of the present disclosure, the intensity variation of the integrated light intensity diffused through sides of the fiber at the illumination wavelength is less than about 30% for the target length of the fiber, which can be, for example, between about 0.02 meters to about 100 meters. The integrated light intensity diffused through sides of the fiber at a specified illumination wavelength can be varied by incorporating fluorescent material in the cladding or coating. The wavelength of the light scattering by the fluorescent material is different from the wavelength of the light propagating in the fiber.

Fiber designs described herein include a nano-structured fiber region (region with nano-sized structures) placed in the core area of the fiber, or very close to the core. The fiber have scattering losses in excess of about 50 dB/km, for example, greater than about 100 dB/km, greater than about 200 dB/km, greater than about 500 dB/km, greater than about 1000 dB/km, greater than about 3000 dB/km, or even greater than about 5000 dB/km. The scattering loss, and thus illumination, or light radiated by the fiber, is uniform in angular space.

In order to reduce or to eliminate bright spots as bends in the fiber, it is desirable that the increase in attenuation at a 90° bend in the fiber is less than about 5.0 dB/turn, for example, less than about 3.0 dB/turn, less than about 2.0 dB/turn, or even less than about 1.0 dB/turn when the bend diameter is less than about 50 mm. In exemplary embodiments, these low bend losses are achieved at even smaller bend diameters, for example, less than about 20 mm, less than about 10 mm, or even less than about 5.0 mm. The total increase in attenuation may be less than about 1.0 dB per 90 degree turn at a bend radius of about 5.0 mm.

The bending loss is equal to or is less than the intrinsic scattering loss from the core of the straight fiber. The intrinsic scattering is predominantly due to scattering from the nano-sized structures. Thus, according to at least the bend insensitive embodiments of optical fiber, the bend loss does not exceed the intrinsic scattering of the fiber. However, because scattering level is a function of bending diameter, the bending deployment of the fiber depends on its scattering level. For example, the fiber may have a bend loss of less than about 3.0 dB/turn, or even less than about 2.0 dB/turn, and the fiber can be bent in an arc with a radius as small as about 5.0 mm without forming bright spots.

According to some embodiments, the light diffusing fiber 12 includes a core at least partially filled with nanostructures for scattering light, a cladding surrounding the core, and at least one coating surrounding the cladding. For example, the core and cladding may be surrounded by primary and secondary coating layers, and/or by an ink layer. In some embodiments, the ink layer contains pigments to provide additional absorption and modify the spectrum of the light scattered by the fiber (e.g., to provide additional color(s) to the diffused light). In other embodiments, one or more of the coating layers comprises molecules which convert the wavelength of the light propagating through the fiber core such that the light emanating from the fiber coating (light diffused by the fiber) is at a different wavelength. In some embodiments, the ink layer and/or the coating layer may comprise phosphor in order to convert the scattered light from the core into light of differing wavelength(s). In some embodiments, the phosphor and/or pigments are dispersed in the primary coating. In some embodiments the pigments are dispersed in the secondary coating, in some embodiments the pigments are dispersed in the primary and secondary coatings. In some embodiments, the phosphor and/or pigments are dispersed in the polymeric cladding. Preferably, the nanostructures are voids filled $SO_2$.

According to some embodiments, the optical fiber 12 includes a primary coating, an optional secondary coating surrounding the primary coating and/or an ink layer (for example located directly on the cladding, or on one of the coatings. The primary and/or the secondary coating may comprise at least one of: pigment, phosphors, fluorescent material, UV absorbing material, hydrophilic material, light modifying material, or a combination thereof.

According to some embodiments, a light diffusing optical fiber includes: (1) a glass core, a cladding, and a plurality of nano-sized structures situated within said core or at a core-cladding boundary, the optical fiber further including an outer surface and is configured to (i) scatter guided light via said nano-sized structures away from the core and through the outer surface, (ii) have a scattering-induced attenuation greater than 50 dB/km at illumination wavelength; and (2) one or more coatings, such that either the cladding or at least one coating includes phosphor or pigments. According to some embodiments, these pigments may be capable of altering the wavelength of the light such that the illumination (diffused light) provided by the outer surface of the fiber is of a different wavelength from that of the light propagating through fiber core. Preferably, the nanostructures are voids filled SO2.

According to some embodiments, a light diffusing optical fiber includes: a glass core, a cladding, and a plurality of nano-sized structures situated within said core or at a core-cladding boundary. The optical fiber further includes an outer surface and is configured to (i) scatter guided light via said nano-sized structures away from the core and through the outer surface, (ii) have a scattering-induced attenuation greater than 50 dB/km at illumination wavelength; wherein the entire core includes nano-sized structures. Such fiber may optionally include at least one coating, such that either the cladding or at least one coating includes phosphor or pigments. According to some embodiments the nanostructures are voids filled $SO_2$.

According to some embodiments, a light diffusing optical fiber includes: a glass core, and a plurality of nano-sized structures situated within said core such that the entire core includes nano-structures, the optical fiber further including an outer surface and is configured to (i) scatter guided light via said nano-sized structures away from the core and through the outer surface, (ii) have a scattering-induced attenuation greater than 50 dB/km at illumination wavelength, wherein the fiber does not include cladding. According to some embodiments, the nanostructures are voids filled $SO_2$. The $SO_2$ filled voids in the nano-structured area greatly contribute to scattering (improve scattering).

According to some embodiments, a light diffusing optical fiber includes: a glass core, and a plurality of nano-sized structures situated within said core such that the entire core includes nano-structures, said optical fiber further including an outer surface and is configured to (i) scatter guided light via said nano-sized structures away from the core and through the outer surface, (ii) have a scattering-induced attenuation greater than 50 dB/km at illumination wavelength wherein said fiber does not include cladding. According to some embodiments, the fiber includes at least one coating such that either the cladding or the coating includes phosphor or pigments. According to some embodiments, the nanostructures are voids filled $SO_2$. As stated above, the $SO_2$ filled voids in the nano-structured area greatly contribute to scattering (improve scattering).

Figure 2:
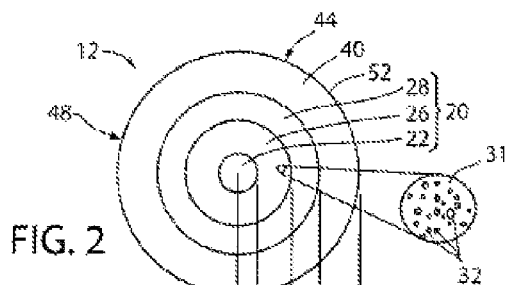
FIG. 2 is a schematic cross-section of the optical fiber of FIG. 1 as viewed along the direction 2-2.

FIG. 1 is a schematic side view of a section of a light diffusing fiber with a plurality of voids in the core of the light diffusing optical fiber 12 having a central axis, or centerline 16. FIG. 2 is a schematic cross-section of light diffusing optical fiber 12 as viewed along the direction 2-2 in FIG. 1. Light diffusing optical fiber 12 can be, for example, any one of the various types of optical fiber with a nano-structured fiber region having periodic or non-periodic nano-sized structures 32. As an example, fiber 12 includes a core 20 divided into three sections or regions. The sections or regions include a solid central region 22, a nano-structured ring portion 26, and an outer, solid portion 28 surrounding the nano-structured ring portion 26. A cladding 40 surrounds the core 20 and has an outer surface. The cladding 40 can be, for example, a low index polymer such as UV or thermally curable fluoroacrylate or silicone. The cladding 40 may include pure low index polymer. Additionally, the cladding 40 may also include pure or F-doped silica. The cladding 40 may have low refractive index to provide a high numerical aperture (NA). The NA of fiber 12 may be equal to, or greater than, the NA of a light source directing light into the fiber 12. According to embodiments of the present disclosure, the NA of fiber 12 may be greater than about 0.2, greater than about 0.3, or even greater than about 0.4.

According to exemplary embodiments, the nano-structured ring portion 26 of light diffusing fiber 12 comprises a glass matrix 31 with a plurality of non-periodically disposed nano-sized structures 32 situated therein, such as the example voids shown in detail in the magnified inset of FIG. 2. The voids may be periodically disposed, such as in a photonic crystal optical fiber, wherein the voids typically have diameters between about $1.0 \times 10^{-6}$ m and about $1.0 \times 10^{-5}$ m. The diameters of the voids may be at least about 10 nm. The voids may also be non-periodically or randomly disposed. The glass matrix 31 in nano-structured ring portion 26 may be for example, but without limitation, a fluorine-doped silica or an undoped pure silica.

The nano-sized structures 32 scatter the light away from the core 20 and toward the outer surface of the fiber. The scattered light is then diffused through the outer surface of the fiber 12 to provide illumination. That is, most of the light is diffused via scattering through the sides of the fiber 12 along the fiber length. According to embodiments of the present disclosure, the fiber emits substantially uniform radiation over its length, and the fiber has a scattering-induced attenuation of greater than about 50 dB/km in the illumination wavelength. The scattering-induced attenuation may be greater than about 100 dB/km, greater than about 500 dB/km, greater than about 1000 dB/km, greater than about 2000 dB/km, or even greater than about 5000 dB/km in the illumination wavelength. Such scattering losses are about 2.5 to about 250 times greater than the Rayleigh scattering losses in standard single mode and multimode optical fibers. The amount of the loss via scattering can be increased by changing the properties of the fiber 12, the width of the nano-structured region 26, and the size and the density of the nano-sized structures 32.

In some embodiments, nano-structured region 26 includes pure silica including a plurality of nano-sized structures 32. The minimum relative refractive index and the average effective relative refractive index of nano-structured region 26, taking into account the presence of any voids, may both be less than about −0.1%. The nano-sized structures 32, or voids, may contain one or more gases, such as argon, nitrogen, oxygen, krypton, or $SO_2$ or can contain a vacuum with substantially no gas. However, regardless of the presence or absence of any gas, the average refractive index in nano-structured region 26 is lowered due to the presence of nano-sized structures 32. Nano-sized structures 32 can be randomly or non-periodically disposed in the nano-structured region 26. Alternatively, nano-sized structures 32 may be disposed periodically in the nano-structured region 26.

According to exemplary embodiments, solid central region 22 may include germania doped silica, core inner annular region 28 may include pure silica, and the cladding 40 may include a glass or a low index polymer. The nano-structured region 26 may include a plurality of nano-sized structures 32 in pure silica, or, alternatively, nano-structured region 26 may include a plurality of nano-sized structures 32 in fluorine-doped silica. According to other exemplary embodiments, the entire core 20 may be nano-structured (filled with voids, for example), with the core 20 being surrounded by the cladding 40. The core 20 may have a "step" refractive index delta, or may have a graded core profile, with a-profile having, for example, α-value between about 1.8 and about 2.3.

Glass in solid central region 22 and core inner annular region 28 may include updopants, such as Ge, Al, Ti, P and combinations thereof. By "non-periodically disposed" or "non-periodic distribution," it is meant that when one takes a cross-section of the optical fiber, such as shown in FIG. 2, the nano-sized structures 32 are randomly or non-periodically distributed across a portion of the fiber. As an example, where the nano-sized structures 32 include voids, similar cross-sections taken at different points along the length of the fiber will reveal different cross-sectional void patterns, i.e., various cross-sections will have different voids patterns, wherein the distributions of voids and sizes of voids do not match. That is, the voids are non-periodic, i.e., they are not periodically disposed within the fiber structure. These voids are stretched (elongated) along the length (i.e. parallel to the longitudinal axis) of the optical fiber, but do not extend the entire length of the entire fiber for typical lengths of transmission fiber. The voids may extend less than about 10 meters, and in many cases less than about 1.0 meter along the length of the fiber 12.

As described above, solid central region 22 and core inner annular region 28 may include silica doped with germanium, i.e., germania-doped silica. Dopants other than germanium, singly or in combination, may be employed within the core, and particularly at or near the centerline 16, of the optical fiber 12 to obtain the desired refractive index and density. The relative refractive index profile of the optical fiber 12 disclosed herein is non-negative in core sections solid central region 22 and core inner annular region 28. The optical fiber may contain no index-decreasing dopants in the core. Additionally, the relative refractive index profile of the optical fiber 12 may be non-negative in solid central region 22, nano-structured ring portion 26 and/or core inner annular region 28.

The fiber 12 optionally includes a coating 44 surrounding the cladding 40. Coating 44 may include a low modulus primary coating layer and a high modulus secondary coating layer. The coating 44 may be a polymer coating such as an acrylate-based or silicone based polymer. The coating may have a constant diameter along the length of the fiber. The coating 44 may be designed to enhance the distribution and/or the nature of light that passes from core 20 through cladding 40. The outer surface of the cladding 40 or the outer surface or the optional coating 44 represents the sides 48 of fiber 12 through which light traveling in the fiber exits via scattering, as described herein.

According to embodiments of the present disclosure, core 20 may be a graded-index core, and may have a refractive index profile having a parabolic (or substantially parabolic) shape. For example, the refractive index profile of core 20 may have an α-shape with an α value of about 2.0 as measured at 850 nm. The a value may be between about 1.8 and about 2.3. According to other exemplary embodiments, one or more segments of the refractive index profile may have a substantially step index shape with an α value greater than about 8.0, or greater than about 10, or even greater than about 20, as measured at 850 nm. The refractive index of the core may have a centerline dip, wherein the maximum refractive index of the core 20, and the maximum refractive index of the entire optical fiber 12, is located a small distance away from centerline 16. Alternatively, the refractive index of the core 20 has no centerline dip, and the maximum refractive index of the core 20, and the maximum refractive index of the entire optical fiber 12, is located at the centerline. According to exemplary embodiments, the refractive index of fiber 12 may have radial symmetry.

According to embodiments of the present disclosure, fiber 12 has a silica-based core 20 and depressed index (relative to silica) polymer cladding 40. The low index polymer cladding 40 may have a relative refractive index that is negative. For example, the relative refractive index of the low index polymer cladding 40 may be less than about −0.5%, or even less than about −1.0%. The cladding 40 may have a thickness of greater than about 20 μm, and the outer diameter of the cladding 40 may have a constant diameter along the length of fiber 12. The cladding 40 may have a lower refractive index than the core 20, and a thickness of greater than about 10 μm. The cladding 40 may have an outer diameter of $2 \times R_{max}$. For example, the cladding 40 may have an outer diameter of about 125 μm, such as between about 120 μm and 130 μm, or between about 123 μm and about 128 μm. Alternatively, the cladding 40 may have a diameter that is less than about 120 μm, such as between about 60 μm and about 80 μm.

The outer diameter 2R3 of core 20 may be constant along the length of the fiber 12. Additionally, the outer diameters of solid central region 22, nano-structured ring portion 26 and core inner annular region 28 may also be constant along the length of the fiber 12. By constant, it is meant that the variations in the diameter with respect to the mean value are, for example, less than about 10%, or less than about 5.0%, or even less than about 2.0%.

Figure 3A:
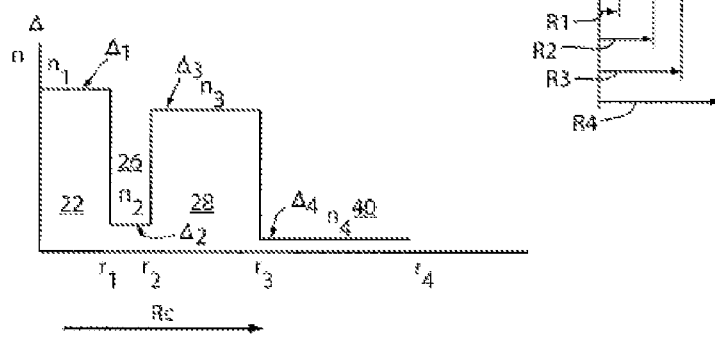
FIG. 3A is a schematic illustration of relative refractive index plot versus fiber radius for an exemplary embodiment of light diffusing fiber.

The outer radius $R_c$ of core 20 may be greater than about 10 μm and less than about 600 μm, for example, between about 30 μm and about 400 μm, or between about 125 μm and about 300 μm. The outer radius $R_c$ of core 20 may be between about 50 μm and about 250 μm. As shown in FIG. 3A, the outer radius $R_c$ of core 20 is equal to the outer radius $R_3$ of core inner annular region 28.

The solid central region 22 may have a radius $R_1$ such that $0.1R_c \leq R_1 \leq 0.9 R_c$, or such that $0.5R_c \leq R_1 \leq 0.9R_c$. $R_1$ may be between about 24 μm and about 50 μm such that the diameter of the solid central region 22 is between about 48 μm and 100 μm. For example, $R_1$ may be greater than about 24 μm, greater than about 30 μm, or even greater than about 40 μm. The nano-structured ring region 26 may have a width $W_2$ such that $0.05R_c \leq W_2 \leq 0.9R_c$, or such that $0.1R_c \leq W_2 \leq 0.9R_c$. Additionally, width $W_2$ may be $0.5R_c \leq W_2 \leq 0.9R_c$. According to embodiments of the present disclosure, a wider nano-structured region 26 provides a higher scattering-induced attenuation for the same density of nano-sized structures 32. The radial width $W_2$ of nano-structured region 26 may be greater than about 1.0 μm. For example, $W_2$ may be between about 5.0 μm and about 300 μm, such as less than about 200 μm. $W_2$ may also be, for example, between about 2.0 μm and about 100 μm, between about 2.0 μm and about 50 μm, between at least 2.0 μm and about 20 μm, or even between about 2.0 μm and about 12 μm. $W_2$ may be, for example, at least about 7.0 μm. The core inner annular region 28 may have a width $W_3$ such that $W_3 = R_3 - R_2$ and has a midpoint $R_{3MID} = (R_2 + R_3)/2$. The core inner annular region 28 may have a width $W_3$ such that $0.1R_c > W_3 > 0.9R_c$. For example, $W_3$ may be between about 1.0 μm and about 100 μm. Additionally, the cladding 40 has a radius $R_4$, which is also the outermost periphery of the optical fiber 12. The width of the cladding 40, which is equal to $R_4 - R_3$, may be, for example, greater than about 20 μm, or greater than about 50 μm, or even greater than about 70 μm.

FIG. 3A is a plot of the exemplary relative refractive index Δ versus fiber radius for an example fiber 12 shown in FIG. 2 (solid line). The core 20 may also have a graded core profile, with a-profile having, for example, α-value between about 1.7 and about 2.3 (e.g., about 1.8 to about 2.3). Solid central region 22 extends radially outwardly from the centerline to its outer radius, $R_1$, and has a relative refractive index profile $\Delta_1(r)$ corresponding to a maximum refractive index $n_1$ (and relative refractive index percent $\Delta_{1MAX}$). According to the embodiment of FIG. 3A, the reference index $n_{REF}$ is the refractive index at the cladding. The nano-structured region 26 has minimum refractive index $n_2$, a relative refractive index profile $\Delta_2(r)$, a maximum relative refractive index $\Delta_{2MAX}$, and a minimum relative refractive index $\Delta_{2MIN}$, wherein some embodiments $\Delta_{2MAX}=\Delta_{2MIN}$. The core inner annular region 28 has a maximum refractive index $n_3$, a relative refractive index profile $\Delta_3(r)$ with a maximum relative refractive index $\Delta_{3MAX}$ and a minimum relative refractive index $\Delta_{3MIN}$, wherein some embodiments $\Delta_{3MAX}=\Delta_{3MIN}$. As further shown in FIG. 3A, the cladding 40 has a refractive index $n_4$, a relative refractive index profile $\Delta_4(r)$ with a maximum relative refractive index $\Delta_{4MAX}$ and a minimum relative refractive index $\Delta_{4MIN}$. In some embodiments, $\Delta_{4MAX}=\Delta_{4MIN}$. In some embodiments, $\Delta_{1MAX}>\Delta_{4MAX}$ and $\Delta_{3MAX}>\Delta_{4MAX}$. In some embodiments $\Delta_{2MIN}>\Delta_{4MAX}$. In the embodiment shown in FIGS. 2 and 3A, $\Delta_{1MAX}>\Delta_{3MAX}>\Delta_{2MAX}>\Delta_{4MAX}$, and the refractive indices of the regions have the following relationship $n_1>n_3>n_2>n_4$.

Solid central region 22 and core inner annular region 28 may have a substantially constant refractive index profile, as shown in FIG. 3A with a constant $\Delta_1(r)$ and $\Delta_3(r)$. In addition, $\Delta_2(r)$ may be either slightly positive ($0<\Delta_2(r)<0.1\%$), negative ($-0.1\%<\Delta_2(r)<0$), or substantially constant. The absolute magnitude of $\Delta_2(r)$ may be less than about 0.1%, for example, less than about 0.05%. According to embodiments of the present disclosure, absolute magnitude of $\Delta_2(r)$ may be less than about 0.025%, or even less than about 0.01%, for more than about 50% of the radial width of the nano-structured ring portion 26. The cladding 40 may have a substantially constant refractive index profile, as shown in FIG. 3A with a constant $\Delta_4(r)$, where $\Delta 4(r)=0\%$. In some embodiments the cladding 40 may have a refractive index $-0.05\%<\Delta_4(r)<0.05\%$. The solid central region 22 may have a refractive index where $\Delta_1(r)>0\%$. Additionally, nano-structured ring portion 26 may have a relative refractive index profile $\Delta 2(r)$ having a negative refractive index with absolute magnitude less than about 0.05%, and $\Delta_3(r)$ of core inner annular region 28 may be, for example, positive or zero. In at least some embodiments, $n_1>n_2$ and $n_3>n_4$.

Figure 3B:
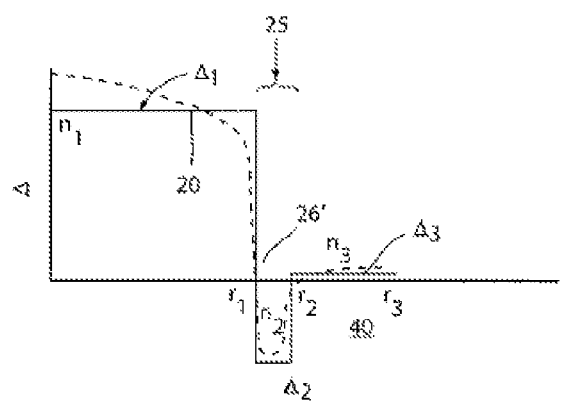
FIG. 3B is a schematic illustration of relative refractive index plot versus fiber radius for another exemplary embodiment of light diffusing fiber.

FIG. 3B schematically illustrates an exemplary embodiment of light diffusing fiber 12. As shown, the fiber 12 includes a core 20 with a relative refractive index $\Delta_1$ and a nano-structured region 26' situated over and surrounding the core 20. The core 20 may have a step index profile, or a graded core profile, with a-profile having, for example, α-value between about 1.8 and about 2.3. The nano-structured region 26' is an annular ring with a plurality of voids. The width of nano-structured region 26' may be as small as about 1.0 µm to about 2.0 µm, and may have a negative average relative refractive index $\Delta_2$. The cladding 40 surrounds the nano-structured region 26', the cladding 40 having a width that may be as small as about 1.0 µm. The cladding 40 may have a negative, a positive or a substantially constant relative refractive index. The main difference between the examples shown in FIGS. 3A and 3B is that nano-structured region 26 shown in FIG. 3A is located in the core 20 of the light diffusing fiber 12, and nano-structured region 26' shown in FIG. 3B is located at the interface of the core 20 and the cladding 40. In the direction moving radially outwardly from the centerline, the nano-structured region 26' begins where the relative refractive index of the core first reaches a value of less than about −0.05%. In the embodiment shown in FIG. 3B, the cladding 40 has a relative refractive index profile $\Delta_3(r)$ having a maximum absolute magnitude less than about 0.1%, where $\Delta_{3MAX}\leq0.05\%$ and $\Delta_{3MIN}>-0.05\%$, and the nano-structured region 26' ends where the outmost void occurs in the void-filled region. Additionally, as shown in FIG. 3B, the index of refraction of the core 20 is greater than the index of refraction $n_2$ of the nano-structured region 26', and the index of refraction $n_1$ of the cladding 40 is also greater than the index of refraction $n_2$ of nano-structured region.

Figure 3C:
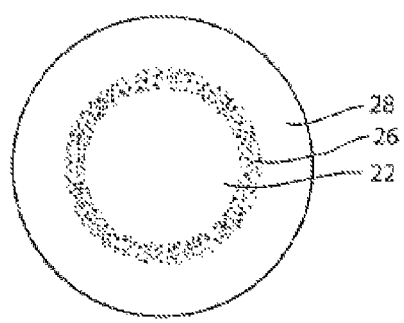
FIG. 3C illustrates another exemplary embodiment of a light diffusing fiber.

FIG. 3C illustrates an embodiment of an optical fiber 12 in accordance with the present disclosure. The fiber 12, which was made, has a core region 22, a nano-structured region 26, a third core region 26 and a polymer cladding 40. The fiber 12 had a first core region 22 with an outer radius $R_1$ of about 33.4 µm, a nano-structured region 26 with an outer radius $R_2$ of about 42.8 µm, a third core region 28 with an outer radius $R_3$ of about 62.5 µm, and a polymer cladding 40 (not shown) with an outer radius $R_4$ of about 82.5 µm. The material of the core was pure silica, the material of the cladding 40 was a low index polymer (e.g., UV curable silicone having a refractive index of 1.413 commercially available from Dow-Corning of Midland, Mich. under product name Q3-6696). The fiber 12 had an NA of 0.3. The fiber 12 included nano-sized structures containing $SO_2$ gas. Applicants found that filled $SO_2$ voids in the nano-structured ring 26 greatly contribute to scattering. Furthermore, when $SO_2$ gas was used to form the nano-structures, it has been discovered that this gas allows a thermally reversible loss to be obtained, i.e., below 600° C. the nano-structured fiber scatters light, but above 600° C. the same fiber will guide light. This unique behavior that $SO_2$ imparts is also reversible, in that upon cooling the same fiber below 600° C., the fiber 12 will act as light diffusing fiber and will again generate an observable scattering effect.

The light diffusing fiber 12 according to embodiments of the present disclosure can be made by methods which utilize preform consolidation conditions which result in a significant amount of gases being trapped in the consolidated glass blank, thereby causing the formation of voids in the consolidated glass optical fiber preform. Rather than taking steps to remove these voids, the resultant preform is used to form an optical fiber with voids, or nano-sized structures, therein. The resultant fiber's nano-sized structures or voids are utilized to scatter or guide the light out of the fiber, via its sides, along the fiber length. That is, the light is guided away from the core 20, through the outer surface of the fiber, to provide desired illumination.

As used herein, the diameter of a nano-sized structure such as a void is the longest line segment contained within the nano-sized structure whose endpoints are at the boundary of the nano-sized structure when the optical fiber is viewed in perpendicular cross-section transverse to the longitudinal axis of the fiber. A method of making optical fibers with nano-sized voids is described, for example, in U.S. Patent Application Publication No. 2007/0104437 A1, which is incorporated herein by reference.

According to embodiments of the present disclosure, light diffusing fiber 12 provides uniform illumination along the length of the fiber 12. The light scattering axially from the surface of the fiber has a variation relative to the mean scattering intensity that is less than about 50%, less than about 30%, less than about 20%, or even less than about 10%. The dominant scattering mechanism in conventional silica-based optical fibers without nano-sized structures is Rayleigh scattering, which has a broad angular distribution. The uniformity of illumination along the fiber length may be controlled such that the minimum scattering illumination intensity is not less than about 0.7 of the maximum scattering illumination intensity. As described below, such minimum scattering illumination intensity may be achieved by controlling fiber tension during the draw process, or by selecting the appropriate draw tension. Appropriate draw tensions may be, for example, between about 30 g and about 100 g, or between about 40 g and about 90 g.

Figure 4A:
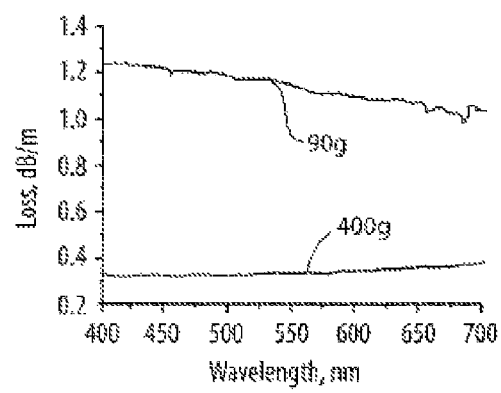
FIGS. 4A and 4B depict fiber attenuation (loss) in dB/m versus wavelength (nm)
Figure 4B:
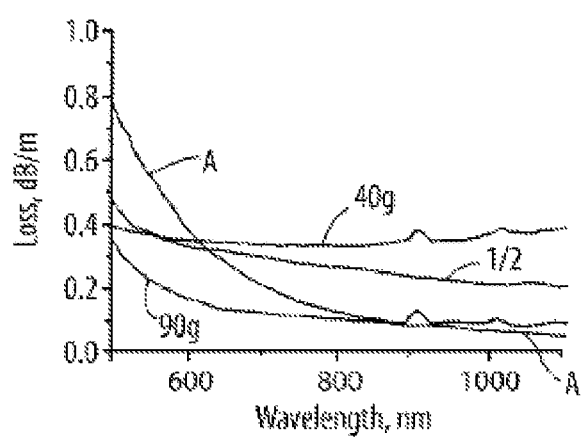

FIG. 4A is a plot of attenuation versus wavelength for a fiber such as shown in FIG. 3C which included $SO_2$ gas filled voids. The figure depicts attenuation as a function of wavelength for a light diffusing fiber 12 drawn at a tension of 90 g and a light diffusing fiber 12 drawn at a tension of 400 g. FIG. 4A illustrates that light diffusing fibers 12 can achieve very large scattering losses, and thus can provide high illumination intensity, in the visible wavelength range. More specifically, FIG. 4A illustrates that higher fiber draw tensions result in lower scattering losses and that lower fiber draw tensions result in a fiber section with higher scattering loss, and thus, stronger illumination.

FIG. 4B is a plot of attenuation versus wavelength for a light diffusing fiber 12 drawn at a tension of 90 g, a light diffusing fiber 12 drawn at a tension of 40 g, a comparative multiple mode fiber (labeled fiber A) with normalized loss, and a theoretical fiber having a loss dependence of $1/\lambda$. The light diffusing fibers 12 shown in FIG. 4B included nano-sized structures containing $SO_2$ gas. (The graph of FIG. 4B depicts wavelength dependence of the loss. In this example, in order to compare the slope of the scattering for the light fiber 12 and fiber A, the loss of low loss fiber (fiber A) was multiplied by a factor of 20, so that the two plots can be easily shown in the same Figure). As shown, the average spectral attenuation from 400 nm to 1100 nm was about 0.4 dB/m for the fiber drawn with a tension of about 40 g, and was about 0.1 dB/m for the fiber drawn with a tension of about 90 g. FIG. 4B illustrates that optical fiber 12 has a relatively flat (weak) dependence on wavelength as compared to standard single-mode transmission fiber, such as for example, SMF-28e$^R$ fiber. In standard single mode or multimode optical fibers, the losses at wavelengths less than about 1300 nm are dominated by Rayleigh scattering. These Rayleigh scattering losses are determined by the properties of the material and are typically about 20 dB/km for visible wavelengths between about 400 n and about 700 nm where Rayleigh scattering losses are proportional to $\lambda^{-p}$, where p is about 4. In contrast, light diffusing fiber 12 according to the present disclosure, have scattering losses proportional to $1/\lambda^{-p}$, where p is less than 2, less than 1, or even more less than 0.5. According to embodiments of the present disclosure, p may be less than 2, less than 1, or even more less than 0.5 over at least about 80% of the wavelength range of 400 nm-1100 nm.

Without being bound to any particular theory, it is believed that the increase in the scattering losses when the draw tension decreases, for example from about 90 g to about 40 g, is due to an increase in the average diameter of the nanostructures. Therefore, this effect of fiber tension could be used to produce constant attenuation along the length of the fiber by varying the fiber tension during the draw process. For example, a first fiber segment drawn at high tension, $T_1$, with a loss of $\alpha_1$ and length, $L_1$, will attenuate the optical power from an input level P0 to P0 exp($-\alpha_1 * L_1/4.343$). A second fiber segment optically coupled to the first fiber segment and drawn at lower tension $T_2$ with a loss of $\alpha_2$ and length $L_2$ will further attenuate the optical power from P0 exp($-\alpha_1 * L_1/4.343$) to P0 exp($-\alpha_1 *_L 1/4.343$) exp($-\alpha_2 * L_2/4.343$). The lengths and attenuations of the first and second fiber segments can be adjusted to provide uniform intensity along the length of the concatenated fiber.

According to embodiments of the present disclosure, the fiber 12 may include a luminophoric ink coating. The luminophoric ink may be a fluorescent material that converts scattered light to a longer wavelength of light. White light may be diffused out of the outer surface of the fiber 12 by coupling the light diffusing fiber 12 with such a coating to a light source. The angular distribution of fluorescence white light in the exemplary embodiments is substantially uniform in angular space. For example, the angular distribution of fluorescence white light is between about 25% and about 400%, or between about 50% and about 200%, or between about 50% and about 150%, or between about 70% and about 130%, or even between about 80% and about 120% in angular space.

Figure 5:
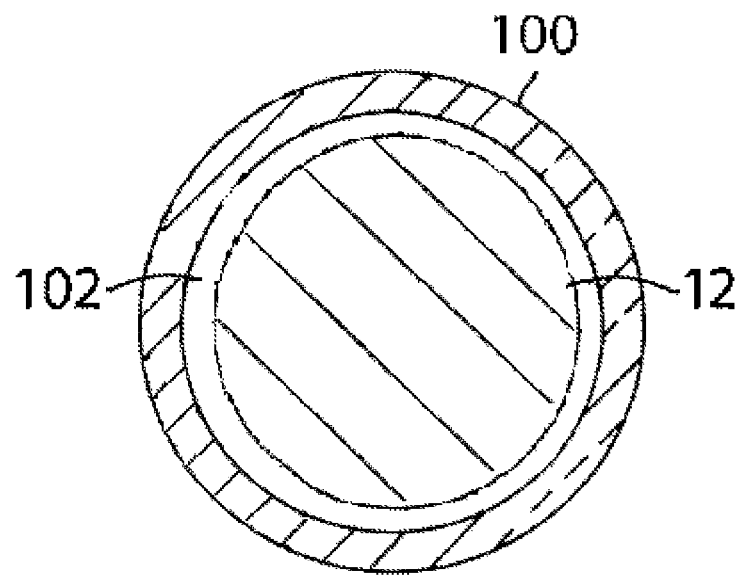
FIG. 5 illustrates a tubular body of an illumination system in accordance with embodiments of the present disclosure.

FIG. 5 illustrates a tubular body 100 of an illumination system in accordance with embodiments of the present disclosure. The tubular body 100 is made of a light permeable material and has a peripheral wall, a distal end, a proximal end, and at least one lumen 102 extending between the distal end and the proximal end. The tubular body 100 may be formed from a flexible material. The flexible material may be a non-rigid medical grade material that facilitates insertion of the tubular body 100 into an orifice of a patient, as well as advancement of at least a portion of the tubular body 100 into the anatomical structure to be illuminated during the surgical procedure. Exemplary anatomical structures that may be illuminated during surgical procedures include, but are not limited to, the ureters, blood vessels, gastrointestinal passageways, bile ducts, lymph passageways, spinal lumens, bronchial passageways and nasal passages.

The at least one lumen 102 of the tubular body 100 has an inner diameter that is large enough to accommodate the light diffusing optical fiber 12. For example, where the fiber 12 has an outer diameter of about 125 μm, the inner diameter of the at least one lumen 102 of the tubular body 100 is greater than about 125 μm. The tubular body 100 is configured to have dimensions that allow for the tubular body 100 to be inserted into anatomical structures of various shapes and sizes. The outer diameter of the tubular body 100 may be configured to limit the overall dimensions of the illumination system. For example, the outer diameter may be less than about 110% of the outer diameter of the fiber 12. Alternatively, the outer diameter may be less than about 105% of the outer diameter of the fiber 12, or even less than about 101% of the outer diameter of the fiber 12. For purposes of illustrating the at least one lumen 102, FIG. 5 shows a gap between the inner diameter of the tubular body 100 and the outer diameter of the fiber 12. However, it should be appreciated that there may be little or no gap between the inner diameter of the tubular body 100 and the outer diameter of the fiber 12 and the fiber 12 may contact the inner diameter of the tubular body 100.

Additionally, the tubular body 100 has a length that allows for insertion of the tubular body 100 into an orifice of a patient, as well as advancement of at least a portion of the tubular body 100 into the anatomical structure to be illuminated during the surgical procedure. For example, the tubular body 100 may have a length of between about 0.02 meters and about 100 meters. More particularly, the tubular body 100 may have a length of between about 0.02 meters and about 3.0 meters. The length of the tubular body 100 may be substantially equal to the length of the light diffusing optical fiber 12. Alternatively, the length of the tubular body 100 may be less than the length of the light diffusing optical fiber 12. Where the length of the tubular body 100 is less than the length of the fiber 12, the additional length portion of the optical fiber 12 would not be inserted into the patient and would be situated outside of the patient during medical procedures and would extend to a location at which the fiber 12 is coupled to the light source.

Figure 6:
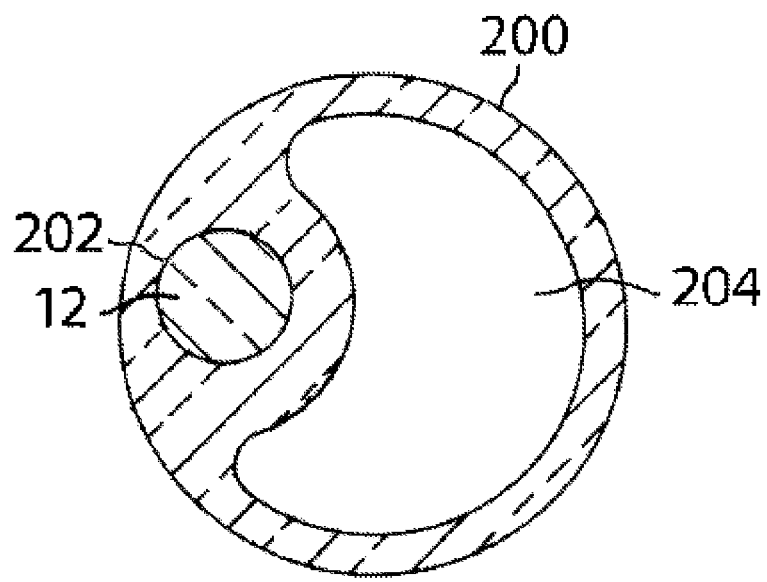
FIG. 6 illustrates a tubular body of an illumination system in accordance with embodiments of the present disclosure.

FIG. 6 illustrates another exemplary tubular body 200 of an illumination system in accordance with embodiments of the present disclosure. The tubular body 200 includes a first lumen 202 configured to accommodate the light diffusing fiber 12 and a second lumen 204 extending between the distal end and the proximal end of the tubular body 200. The second lumen 204 is open at both ends to provide fluid communication between an internal anatomical structure of a patient and an external depository. For example, where the tubular body 200 is introduced into a patient's kidney via the ureter, the second lumen may be used for the drainage of urine from the patient's kidney.

The illumination system also includes a light source. The term "light source" refers to a laser, light emitting diode or other component capable of emitting electromagnetic radiation that is either in the visible light range of wavelengths or is of a wavelength that can interact with a luminophore to emit light in the visible wavelength range. The term "luminophore" refers to an atom or chemical compound that manifests luminescence, and includes a variety of fluorophores and phosphors.

According to embodiments of the present disclosure, light diffusing fiber 12 may include a coating disposed on an end of the light diffusing fiber 12 opposite an end where light from the light source is input into the fiber. The coating may cover at least a portion of the end of the light diffusing fiber 12 such that guided light in the light diffusing fiber 12 is prevented from being transmitted out of the end of the fiber. The coating may cover an end of at least the core and may cover a portion of the surrounding cladding. The coating may be, for example, a reflective coating or an absorptive coating. In certain applications of embodiments of the present disclosure, it may be advantageous to limit the transmission of light from the end of the cylindrical optical diffuser such that substantially all light emitted from the diffuser is emitted through the outer surface of the diffuser.

Optionally, the illumination system may further include a surgical introducer. The introducer is a tube having a high degree of directional control that is used to guide the tubular body into internal anatomical structures of a patient. For example, where the tubular body is introduced into a patient's ureter, the introducer may be used to negotiate the ureter such that the tubular body may be passed therethrough and positioned between the patient's kidney and bladder. The introducer itself may be advanced over a guide wire. The introducer is configured to have sufficient axial strength to be pushed through anatomical structures of a patient via a force applied at its proximal end, but also to have sufficient flexibility to substantially conform to the anatomical structure while also resisting kinking. Additionally, the introducer is configured to have dimensions that allow for it to be inserted into anatomical structures of various shapes and sizes, and also has at least one lumen having an inner diameter that is large enough to accommodate the tubular body.

A method for illuminating an anatomical structure is also provided herein. The method includes inserting at least a portion of a tubular body into the interior of an anatomical structure, wherein the tubular body is made of a light permeable material. The tubular body includes a peripheral wall, a distal end, a proximal end, and at least one lumen extending between the distal end and the proximal end, the at least one lumen having an opening at the distal end and an opening at the proximal end. The tubular body further includes at least one light diffusing optical fiber disposed in the at least one lumen, the at least one light diffusing optical fiber having a core, primary cladding, and a plurality of nano-sized structures, the optical fiber further including an outer surface, and an end optically coupled to a light source. The fiber is configured to scatter guided light via the nano-sized structures away from the core and through the outer surface, to form a light-source fiber portion having a length that emits substantially uniform radiation over its length. The method further includes introducing light from the light source into the end of the at least one light diffusing optical fiber optically coupled to the light source and emitting the light through the outer surface of the fiber to illuminate the light-source fiber portion over its length.

The method may further include illuminating a portion of the anatomical structure such that an operator can avoid contacting the portion of the anatomical structure during a surgical procedure. Alternatively, the method may further include illuminating a portion of the anatomical structure such that an operator can target the portion of the anatomical structure during a surgical procedure. As used herein, illuminating may include transilluminating an anatomical structure such that light emitted from the illuminating system passes through the anatomical structure. Alternatively, illuminating may include directing light emitted from the illuminating system at a surface of an anatomical structure such that light is reflected by the anatomical structure.

The method may further include illuminating a portion of the anatomical structure with short wavelength visible light to disinfect the anatomical structure, or human body substances in the anatomical structure which may contain bacteria. As used herein, the term "short wavelength visible light" is used for a wavelength of light being between about 400 nm and about 500 nm. Recent studies have shown that short wavelength visible light, such as violet and blue light, is lethal to bacteria at certain doses. Such short wavelength visible light may be, for example, between about 400 nm and about 450 nm, or between about 405 nm and about 415 nm. The illuminating light may be used to disinfect, for example, tissue or fluids in or around the anatomical structure to treat conditions caused by the presence of bacteria in the patient. In just one example, the blood vessels of a patient diagnosed with sepsis may be illuminated with short wavelength visible light to reduce or eliminate the bacteria in the patient's blood. Other conditions, such as infections or cysts, may be similarly treated in accordance with the present disclosure.

Embodiments of the present disclosure provide illumination of anatomical structures during surgical procedures. In particular, embodiments provide illumination of anatomical structures during laparoscopic surgical procedures and permit an operator to better visualize the internal cavity of a patient during the minimally invasive procedure.

Embodiments allow the illuminating system, in particular the tubular body, to have thin dimensions and to be flexible. In turn, this provides ease of insertion into an orifice of a patient, as well as advancement of at least a portion of the tubular body into the anatomical structure to be illuminated during the surgical procedure. Additionally, the thin dimensions and flexibility of the embodiments described herein allow for the tubular body to be inserted into anatomical structures of various shapes and sizes. In particular, the tubular body may be thin enough to be inserted into smaller anatomical structures such as, but are not limited to, the ureters, blood vessels, gastrointestinal passageways, bile ducts, lymph passageways, spinal lumens, bronchial passageways and nasal passages.

Additionally, the use of light diffusing optical fiber in accordance with embodiments of the present disclosure provide high illumination intensity in the visible wavelength range and uniform illumination along the length of the light diffusing optical fiber. The high illumination intensity permits clear visualization of illuminated anatomical structures which reduces the risk that an operator will contact the anatomical structure and cause unintended injury during surgical procedures. Similarly, the uniform illumination along the length of the fiber permits clear visualization of the entire anatomical structure, which further reduces the risk of causing unintended injury during surgical procedures. Also, because the light source is provided at a location that is remote from the anatomical structure to be illuminated, embodiments of the present disclosure do not introduce heat into the interior of the patient.

While the embodiments described above discuss certain features that are specific to a particular surgical procedure or to a particular anatomical structure, it should be appreciated that embodiments of the present disclosure are not so limited and that the illuminating system described herein may be advantageously utilized to illuminate anatomical structures during any laparoscopic surgical procedure.

It will be apparent to those skilled in the art that various modifications and variations can be made without departing from the spirit or scope of the invention.

What is claimed is:

1. An illumination system for a surgical device, the illumination system comprising:
   a tubular body made of a light permeable material, the tubular body comprising a peripheral wall, a distal end, a proximal end, and at least two lumens extending between the distal end and the proximal end;
   a light source that generates light having at least one wavelength between 200 nm and 2000 nm; and
   at least one light diffusing optical fiber disposed in at least one of the at least two lumens, the at least one light diffusing optical fiber having a core, primary cladding, and a plurality of nano-sized structures, the optical fiber further including an outer surface, and an end optically coupled to the light source;
   wherein the fiber is configured to scatter guided light via the nano-sized structures away from the core and through the outer surface, to form a light-source fiber portion having a length that emits substantially uniform radiation over its length.

2. The illumination system of claim 1, wherein the light diffusing optical fiber has a scattering-induced attenuation greater than about 50 dB km.

3. The illumination system of claim 1, further comprising a surgical introducer configured to guide the tubular body into an anatomical structure.

4. The illumination system of claim 1, wherein the light diffusing optical fiber radiation is substantially uniform, such that the difference between the minimum and maximum scattering illumination intensity is less than about 30% of the maximum scattering illumination intensity.

5. The illumination system of claim 1, wherein the light diffusing optical fiber has scattering-induced attenuation of about 100 dB/km to about 6,000 dB/km.

6. The illumination system of claim 1, wherein the nano-sized structures are situated within the core or at a core-cladding boundary.

7. The illumination system of claim 1, wherein the entire core comprises nano-sized structures.

8. The illumination system of claim 1, wherein the core of the light diffusing optical fiber comprises silica.

9. The illumination system of claim 6, wherein the nano-sized structures are situated in the core.

10. The illumination system of claim 1, wherein the core of the light diffusing optical fiber comprises silica doped with a dopant selected from the group consisting of germanium and fluorine.

11. The illumination system of claim 1, wherein the cladding comprises either silica based glass or polymer, and wherein the cladding has a thickness of at least about 20 µm.

12. The illumination system of claim 1, further comprising fluorescent and/or scattering species disposed in the coating surrounding the cladding to provide substantially uniform scattering intensity.

13. The illumination system of claim 11, wherein the light source generates light in the 200-500 nm wavelength range and wherein the fluorescent and/or scattering species generates either white, green, red, or near-infrared (NIR) light.

14. The illumination system of claim 1, wherein the nano-sized structures are gas filled voids having a diameter of greater than about 10 nm.

15. The illumination system of claim 1, wherein the plurality of nano-sized structures form a nano-structured region at a core-cladding boundary, the nano-structured region including the nano-sized structures having a width of at least about 7.0 µm, and wherein the cladding has a diameter of at least about 125 µm.

16. The illumination system of claim 1, wherein an end of the at least one light diffusing optical fiber opposite the end optically coupled to the light source is coated with a reflective coating.

17. The illumination system of claim 1, wherein an end of the at least one light diffusing optical fiber opposite the end optically coupled to the light source is coated with an absorptive coating.

18. The illumination system of claim 1, wherein the light source generates light having at least one wavelength between about 400 nm and about 500 nm.

19. A method for illuminating an anatomical structure, the method comprising:
   inserting at least a portion of a tubular body into the interior of an anatomical structure, wherein the tubular body is made of a light permeable material and comprises:
      a peripheral wall, a distal end, a proximal end, and at least one lumen extending between the distal end and the proximal end, the at least one lumen having an opening at the distal end and an opening at the proximal end;
      at least one light diffusing optical fiber disposed in the at least one lumen, the at least one light diffusing optical fiber having a core, primary cladding, and a plurality of nano-sized structures, the optical fiber further including an outer surface, and an end optically coupled to a light source;
      wherein the fiber is configured to scatter guided light via the nano-sized structures away from the core and through the outer surface, to form a light-source fiber portion having a length that emits substantially uniform radiation over its length; and introducing light from the light source into the end of the at least one light diffusing optical fiber optically coupled to the light source and emitting the light through the outer surface of the fiber to illuminate the light-source fiber portion over its length.

20. The method of claim 19, further comprising illuminating a portion of the anatomical structure such that the anatomical structure is transilluminated.

21. The method of claim 19, further comprising illuminating a portion of the anatomical structure such light emitted through the outer surface of the fiber is reflected by the anatomical structure.

22. The method of claim 19, further comprising illuminating a portion of the anatomical structure such that an operator can avoid contacting the portion of the anatomical structure during a surgical procedure.

23. The method of claim 19, further comprising illuminating a portion of the anatomical structure such that an operator can target the portion of the anatomical structure during a surgical procedure.

24. The method of claim 19, wherein the light diffusing optical fiber has a scattering-induced attenuation greater than about 50 dB km.

25. The method of claim 19, wherein introducing light from a light source comprises introducing light having at least one wavelength between about 400 nm and about 500 nm.

26. The method of claim 19, wherein introducing light from the light source is performed while at least a portion of the medical device is positioned in the body of a patient.

27. The method of claim 26, wherein introducing light from a light source comprises introducing light having at least one wavelength between about 400 nm and about 500 nm.

* * * * *